United States Patent [19]
Wang

[11] Patent Number: 6,156,274
[45] Date of Patent: Dec. 5, 2000

[54] OPTICAL MEMBRANE FILMS FOR POLYCATION DETECTION

[75] Inventor: Enju Wang, Flushing, N.Y.

[73] Assignee: St. John's University, Jamaica, N.Y.

[21] Appl. No.: 09/032,503

[22] Filed: Feb. 26, 1998

Related U.S. Application Data

[60] Provisional application No. 60/039,464, Feb. 27, 1997.

[51] Int. Cl.[7] .......................... G01N 21/41; G01N 21/01; G01N 31/16; G01N 21/00; C07D 311/82
[52] U.S. Cl. ...................... 422/82.06; 422/82.05; 422/82.09; 436/163; 436/164; 549/223
[58] Field of Search .............................. 422/82.05, 82.06, 422/82.07, 82.08, 82.09, 82.11; 436/172, 800; 549/223, 224

[56] References Cited

U.S. PATENT DOCUMENTS

| | | | |
|---|---|---|---|
| 5,711,915 | 1/1998 | Siegmund et al. | 422/68.1 |
| 5,756,771 | 5/1998 | Mattingly | 549/223 |
| 5,900,215 | 5/1999 | Seifert et al. | 422/82.07 |

OTHER PUBLICATIONS

W. Tan et al. "Miniaturized fiber–optic chemical sensors with fluorescent dye–doped polymers" Sensors and Actuators B 28 (1995) 157–163.

W. Tan et al. "Development of submicron chemical fiber optic sensors" Anal. Chem. 1992, 64, 2985–2990.

S. Tan et al. "Reversible optical sensing membrane for the determination of chloride in serum" Analytica Chimica Acta, 255 (1991) 35–44.

E. Wang et al. "Calcium optical sensors based on lipophilic anionic dye and calcium–selective organophosphate ionophore or neutral carrier" Analytical Letters, 30(1), 33–44 (1997).

E. Wang et al. "Optical films for protamine detection with lipophilic dichlorofluorescein derivatives" Analytica Chimica Acta 334 (1996) 139–147.

E. Wang et al. "Optical sensors for sodium, potassium and ammonium ions based on lipophilic fluorescein anionic dye and neutral carriers" Analytical Chimica Acta 18466 (1997) 1–6.

E. Wang et al. "Optical detection of macromolecular heparin via selective coextraction into thin polymeric films" Analytical Chemistry, 1995, 34, 522–527.

B. Fu et al. "Polymer membrane–based polyion sensors: development, response mechanism, and bioanalytical applications" Electroanalysis 1995, 7, No. 9, 823–829.

*Primary Examiner*—Jill Warden
*Assistant Examiner*—Dwayne K Handy
*Attorney, Agent, or Firm*—Gifford, Krass, Groh, Sprinkle, Anderson & Citkowski, P.C.

[57] ABSTRACT

Lipophilic fluorescein-based molecules have been synthesized and incorporated into thin plasticized polymeric membrane films as chromoionophores for the optical sensing and detection of polycationic protamine. The membrane response is based on the extraction of protamine into the film due to the interaction between the anionic fluorescein and the protamine polycation which results in a cation exchange between the protamine and proton, and thus, induces an absorbance spectra change of the polymeric film. The response speed is controlled by protamine diffusion through the stagnant diffusion layer adjacent to the film surface as well as within the bulk of the polymer film. When limited exposure time and non-stirring detection modes are used in a buffer solution, absorbance of a film changes as a function of the protamine concentration in the range of about 2 to 60 $\mu$g/ml (0.44 to 13.3 $\mu$M). The sensing film shows good selectivity over most common small cations, it can be used in the determination of protamine in diluted serum or whole blood. No response is observed when a protamine complexing reagent such as heparin is present, thus the instant invention is useful as an indicator for the protamine-heparin titration.

26 Claims, 4 Drawing Sheets

OPTICAL MEMBRANE FILMS FOR POLYCATION DETECTION

RELATED APPLICATION

This application claims benefit of U.S. Provisional Application No. 60/039,464 filed Feb. 27, 1997 which is incorporated herein by reference.

FIELD OF THE INVENTION

This invention relates to a film for optical detection of a polycation and process for producing such a film. More particularly, the invention relates to the detection of protamine and therethrough to molecular species that complex or react with protamine.

BACKGROUND OF THE INVENTION

Thin homogeneous plasticized polymeric membranes (2·5 μm) incorporating lipophilized components (highly selective ionophores) as the chemically acting species have been widely used in developing optical sensors and detectors [1, 2]. These membranes have advantages such as ease of fabrication into various thickness and shapes, high selectivity, sensitivity and reversibility. At present, various polymeric membrane based optical sensors have been successfully developed for small mono- and divalent cations, using cation chromogenic ionophores (chromoionophore) [3–7] or pH indicator and neutral carrier pair ion-exchange systems [8–12]. Ion coextraction systems are employed for reversible anion sensing [13–15]. Recently it has been demonstrated that polymeric membranes incorporated with a specific quaternary ammonium cation and a pH indicator can efficiently extract rather hydrophilic macrosized polyanions such as heparin and DNA. An optical sensing system for the detection of these polyanions has been developed using thin membrane films [16], however, no such system has been developed for the sensing of polycations, such as protamine.

Protamine is a low molecular weight protein (the average MW=4,500) rich in the basic amino acid—arginine [17] and is a polycation at near neutral pH. The guanadinium groups of protamine can complex electrostatically with the sulfonate groups of heparin, and thus it has been used to reverse the anticoagulant effect of heparin near the end of most clinical procedures that use heparin for systematic anticoagulation [18]. Heparin is also used in chronic therapy regimes to prevent deep vein thrombosis and other coagulation disorders. However, excess heparin in a post-surgical or chronic therapy patient increases the danger of "bleeding out" due to slow clotting response. Protamine is known to interact with conventional protein reagents, such as the Folin-phenol reagent and Coomassie Brilliant Blue G-250, and can be measured via either the Lowry [19] or Bradford [20] methods. However, these methods are not specific for protamine. New methods for fast and accurate protamine detection are of great interest. A new dye method for protamine detection in blood or plasma was developed recently, using the competitive binding displacement mechanism between protamine and heparin-azura A dye complex [21]. Furthermore, protamine ion-selective electrodes were developed based on a special formulated PVC poly(vinyl chloride) membrane doped with anionic tetraphenylborates as protamine carriers [22–23].

SUMMARY OF THE INVENTION

The instant invention contains a plasticized polymer membrane based optical sensing system for the detection of polycations, especially for protamine. Since borate, the protamine binder [23], also binds to cationic dyes such as the lipophilic quaternary ammonium cations used in previous cation optical sensing systems [3–8], other anionic dyes were examined as a chromophore. The instant invention utilizes lipophilic fluorescein-like esters containing moderately acidic phenolate groups, the esters which are capable of extracting protamine polycations from aqueous solution into organic membranes. Deprotonation of the fluorescein-like esters due to cation exchange between a polycation and proton causes changes in membrane absorbance. Thus, the lipophilic fluorescein ester is used as protamine polycation carrier and chromophore at the same time (protamine chromoionophore). As described herein, a polymer membrane film doped with a lipophilic ester chromophore responds to micromolar levels of free protamine in solution, therefore it can be used as indicator in the heparin-protamine titration. The high selectivity over the small cations that exist in blood allows the film to be used in monitoring free protamine in diluted/buffered serum.

The instant invention contains a membrane film for optical sensing of a polycation. A lipophilic ester of a compound having the following formula:

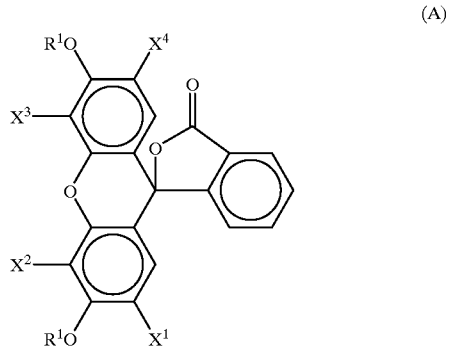

(A)

is optically active to the presence of a polycation; where $X^1$ is a hydrogen atom, a chlorine atom, or a bromine atom; $X^2$ is a hydrogen atom, a chlorine atom, or a bromine atom; $X^3$ is a hydrogen atom, a chlorine atom, or a bromine atom; $X^4$ is a hydrogen atom, a chlorine atom, or a bromine atom and at least one of $X^1$, $X^2$, $X^3$ and $X^4$ is a hydrogen atom; $R^1$ is an alkyl having from 10 to 30 carbon atoms, an alkenyl having from 10 to 30 carbon atoms, a haloalkyl having from 10 to 30 carbon atoms, or a haloalkenyl having from 10 to 30 carbon atoms.

Optionally, for sensing polycations in acidic solutions a lipophilic ester based on fluoresceinamine is utilized in the membrane films of the instant invention. An amine-containing ester of the instant invention has the formula:

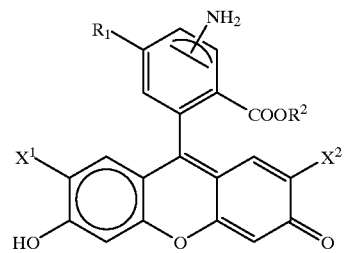

where $R^1$, $x^1$ and $x^2$ are defined as per the lipophilic ester above; $R^2$ is hydrogen, $R^1$ is an alkyl having from 10 to 30 carbon atoms, an alkenyl having from 10 to 30 carbon atoms and at least one of $x^1$ and $x^2$ is a hydrogen atom. The amine group of fluoresceinamine is optionally either meta (isomer I) or para (isomer II) relative to the carboxyl moiety. Preferably, the meta isomer (isomer I) is utilized herein. The optically active ester is mixed with an optically inert polymer and formed as the film.

DETAILED DESCRIPTION OF THE PREFERRED EMBODIMENT

Figure 1:
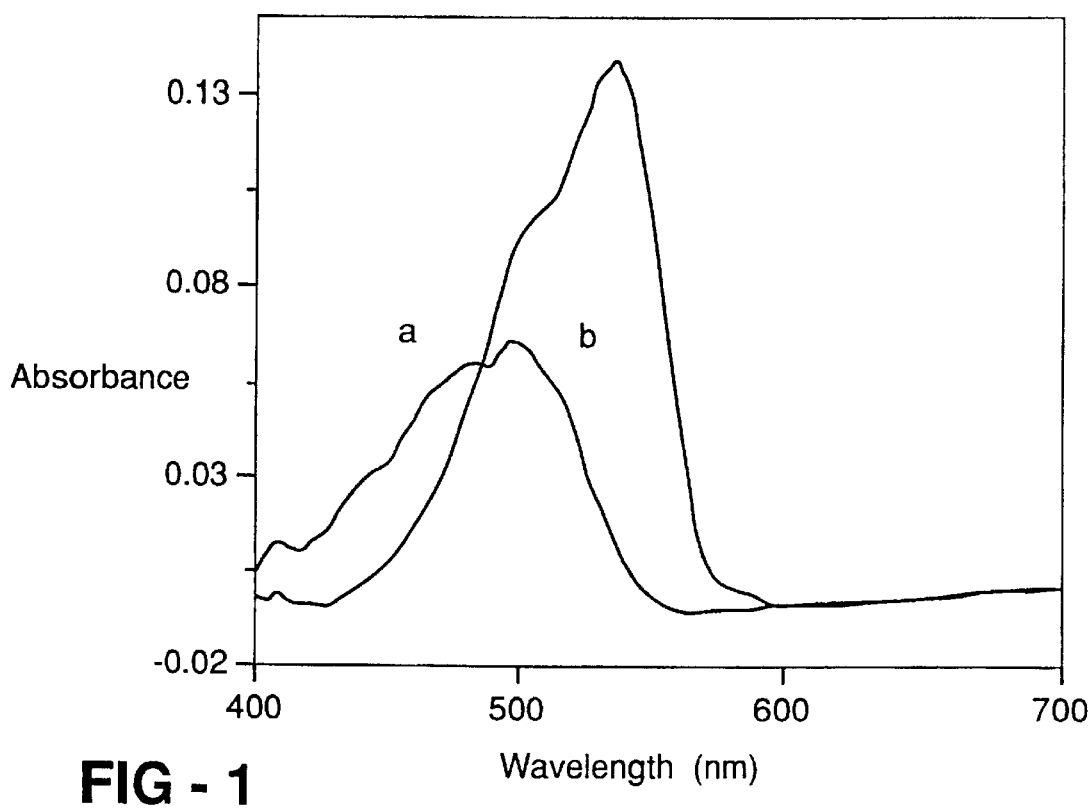
FIG. 1. Absorption spectra of the sensing film (a) before and (b) after exposed to protamine (50 μg/mL) at pH 7.4. Film composition: 1.0 wt. % 2,7-dichlorofluorescein octadecyl ester (2,7-DCFOE), 12.3 wt. % of polyurethane (PU), 15.8 wt. % of poly(vinylchloride) (PVC) and 70.9 wt. % Bis(2-ethylhexyl) sebacate (DOS).

The optical membrane films for polycation detection of the instant invention utilize a synthetic lipophilic fluorescein chromoionophore. A synthesized lipophilic fluorescein chromoionophore (HL) of the instant invention contains an acidic phenolate group (pKa ~4.9) [24] which becomes negatively charged upon deprotonation. The interaction of the negatively charged chromoionophore (L⁻) with the multi-positively charged protamine (hereafter "Prot$^{z+}$") results in the extraction of protamine from aqueous solution into the organic membrane. Cation exchange occurs at suitable pH. The equilibrium between the organic membrane phase and the aqueous solution is described as follows:

$$Prot_{aq}^{z+} + zHL_{org} \rightleftharpoons (Prot-L_z)_{org} + zH_{aq}^+ \qquad (I)$$

Where (Prot-$L_z$) refers to the ion-pair complex between protamine and the chromoionophore, and the subscripts "org" and "aq" refer to the organic membrane and the aqueous phases, respectively. The equilibrium constant $K_{eq}$ depends upon the complex formation constant ($\beta_{Prot-Lz}$), the association constant of L⁻ ($\beta_{HL}$) in the membrane and the distribution coefficients of H⁺ and Prot$^{z+}$ between the organic membrane phase and the aqueous solution ($k_H$ and $k_{prot}$ respectively). Their relation can be expressed as:

$$K_{aq} = \frac{[Prot-L_z][H^+]^z}{[Prot^{z+}][HL]^z} = \frac{(\beta_{Prot-Lz})(K_{Prot})}{(\beta_{HL}K_H)^z} \qquad (1)$$

The membrane absorbance signal A, at the maximum absorbance wavelength of the complex [Prot-$L_z$] correlates with the complex concentration according to A=kz[Prot-$L_2$], where k is related to membrane thickness and the molar absorptivity of the complexed dye in the film. The relative absorbance α defined as the ratio of the concentration of the complexed form ($L_{comp}$=z [Prot-$L_z$]) over the total concentration of the dye [$L_T$] can be deduced as:

$$\alpha = \frac{z[Prot-L_z]}{L_T} = \frac{A-A_0}{A_1-A_0} \qquad (2)$$

and $$\frac{L_T \alpha}{z[L_T(1-\alpha)]^z} = K_{aq} \frac{[Prot^{z+}]}{[H^+]^z} \qquad (3)$$

where $A_0$ and $A_1$ are the limiting absorbance values for α=0 (fully protonated ligand HL) and α=1 (fully complexed ligand), respectively.

Since protamine is highly positively charged (z=~20 at near neutral pH [17]), the optical signal of the sensing film is strongly pH dependent (as per equation 3), and a large change of $C_{prot}$ will induce only a very small change in α for equilibrium response. Preferably, the films of the instant invention operate at a suitable pH for large degree of ion-exchange and a limited sample volume for complete extraction of protamine to the film, i.e. limited volume mode, in order to achieve a high degree of sensitivity for protamine and heparin via interactions therewith. This limited volume mode response principle has been mentioned previously in a study on heparin sensing [16]. At sufficiently high pH, a large degree of ion-exchange occurs, even at low protamine concentrations. Illustratively, as is seen in the examples below, at pH of 7.4, the membrane films with DCFOE as chromoionophore have a significant response to protamine at concentrations as low as 10⁻⁷ M in a limited volume of 20 ml. Operational pH ranges of the instant invention for a particular sample concentration are determined with the assistance of Equation 3. It is appreciated that other polycations may also be quantified using the instant invention provided pH range adjustments are made to account for the polycation charge, isoelectric point, ion-pair equilibrium constant and the like.

Polyurethane/poly(vinyl chloride) (hereafter "PU/PVC") membrane films embodiments of the instant invention doped with the 2,7-dichlorofluorescein ester (DCFOE) therein have maximal absorbances at about 490 nm at pH 7.40, and the absorbance peak shifts to 528 nm with a shoulder at 500 nm at pH of 10.00. At pH 7.40, in the presence of protamine, the absorbance maximum shifts to 536 nm with a shoulder at 510 nm. FIG. 1 shows the absorbance spectra of a thin (~2 μm) PVC/PU film containing 1 wt, % DCFOE in the presence and absence of protamine at pH 7.4. These spectral changes demonstrate a correlation that the negatively charged lipophilic dichlorofluorescein esters have sufficient association affinity to protamine so that they can extract the rather hydrophilic protamine from aqueous solution into the organic film. No detectable leaching is observed in the test solution with the dye content less than 1 wt. % for protamine response (pH <8.5). The chromophore shows severe leaching at pH 10 due to deprotonation, which prevents the film from being used as a pH sensor. Where the polycation of interest is protamine it is preferred that dichlorofluorescein esters are utilized in the active membrane films of the instant invention. It is appreciated that other fluorescein based esterification monomers are more suitable for different polycation detection species.

Corresponding lipophilic docosyl esters of 2,7-dichlorofluorescein; fluorescein; 4,5-dibromofluorescein; fluoresceinamine; and halogenated fluoresceinamines, illustratively including 2-chlorofluoresceinamine, 2,7-dibromofluoresceinamine and 2,7-dichlorofluoresceinamine are also operative in optical detection films for polycations. As expected from the acidity [25], fluorescein esters doped in PVC/PU/DOS films show response only at higher pH (>8.5). 4,5-dibromofluorescein esters and 2,7-dichlorofluorescein docosyl esters (DCFDE) show response comparable to that of the DCFOE based films at pH 7.4. 2,7-dichlorofluorescein esters are discussed specifically hereafter, however it is appreciated that the above mentioned esters are also functional for polycation detection, subject to the pH response of the individual esters. For example, fluorosceinamine based films are generally optimal for polycation detection in the pH range from about 3 to about 4.7. For simple comparison, data shown in all figures and tables are based on DCFOE as the chromoionophore and the film compositions are the same as that given in FIG. 1, and the film thickness is 2±0.2 $\mu$m.

Figure 2:
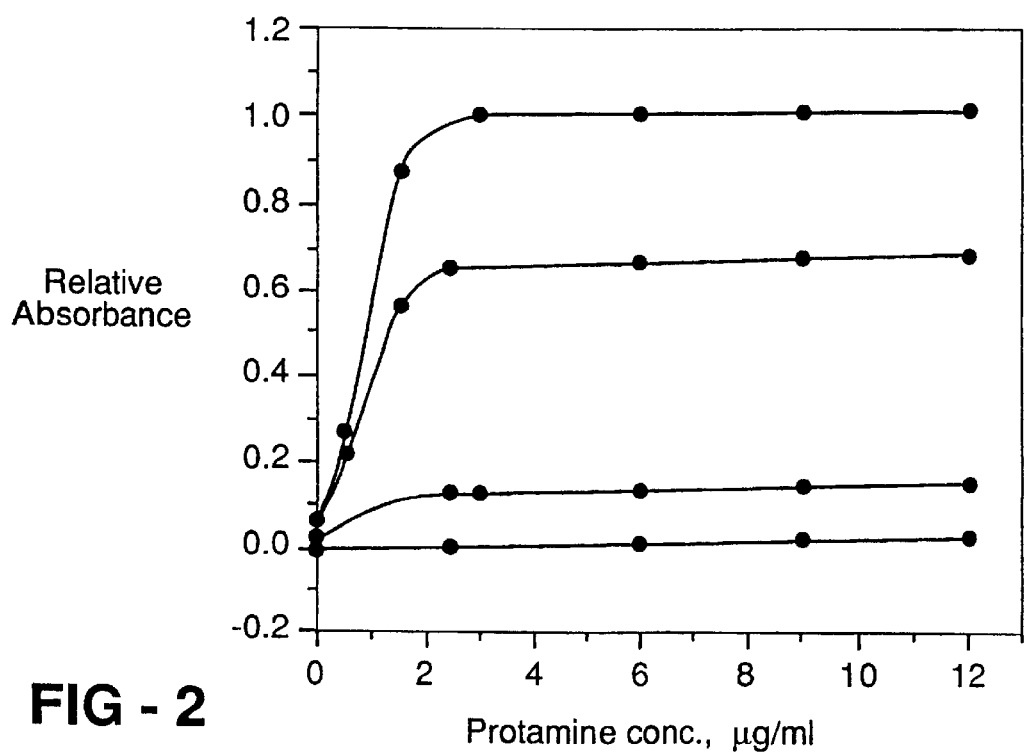
FIG. 2. Influence of solution pH on a 2,7-DCFOE sensing film response to protamine, (○) 6.00, (●) 6.50, (□) 7.00, (▲) 7.40 for the film composition of FIG. 1.

As discussed above in reference to equations 1–3, the response of a membrane film of the instant invention to protamine is strongly influenced by the buffer pH. Hence, the membrane film response to protamine is recorded in buffers of varying pH levels. To ensure equilibrium, the absorbances (at 536 nm) are taken after contact with each solution (20 ml under stirring) for 60 min. For a 1 wt. % 2,7-DCFOE, 12.3 wt. % PU, 15.8 wt. % PVC and 70.9 wt. % DOS optical membrane film of the instant invention, in the pH range of 6.00~6.70, the membrane response time is less than 10 min, and the response is reversible. However, at these pH values, due to proton competition, the film is less sensitive to protamine concentration changes. At pH higher than 7.00, a significant response is observed at protamine levels as low as 0.5 $\mu$g/ml ($10^{-7}$ M) (initial concentration). Membrane films of the instant invention cannot be reversed in a short time in these buffers, but they are easily reversed in a low pH (e.g. 4–5) buffer. This indicates that the interaction between protamine and the chromophore are very fast on a diffusion time scale. The results at four pH levels are illustrated in FIG. 2.

It should be noted that significant response of the instant invention at low protamine levels results in a considerable reduction of protamine concentration in the limited sample volume. The protamine concentration left in the aqueous solution is a very small fraction of the initial protamine concentration. Thus, at pH=7.4, with response time of 1 h under stirring and measurements in a fixed volume of 20 ml, a nearly linear response is obtained at low protamine concentrations (1.5 $\mu$g/ml with 2 $\mu$m membrane). At higher protamine levels (>2.0 $\mu$g/ml), the absorbance reaches a maximum value, which corresponds to an extraction saturation of the thin film.

Figure 3:
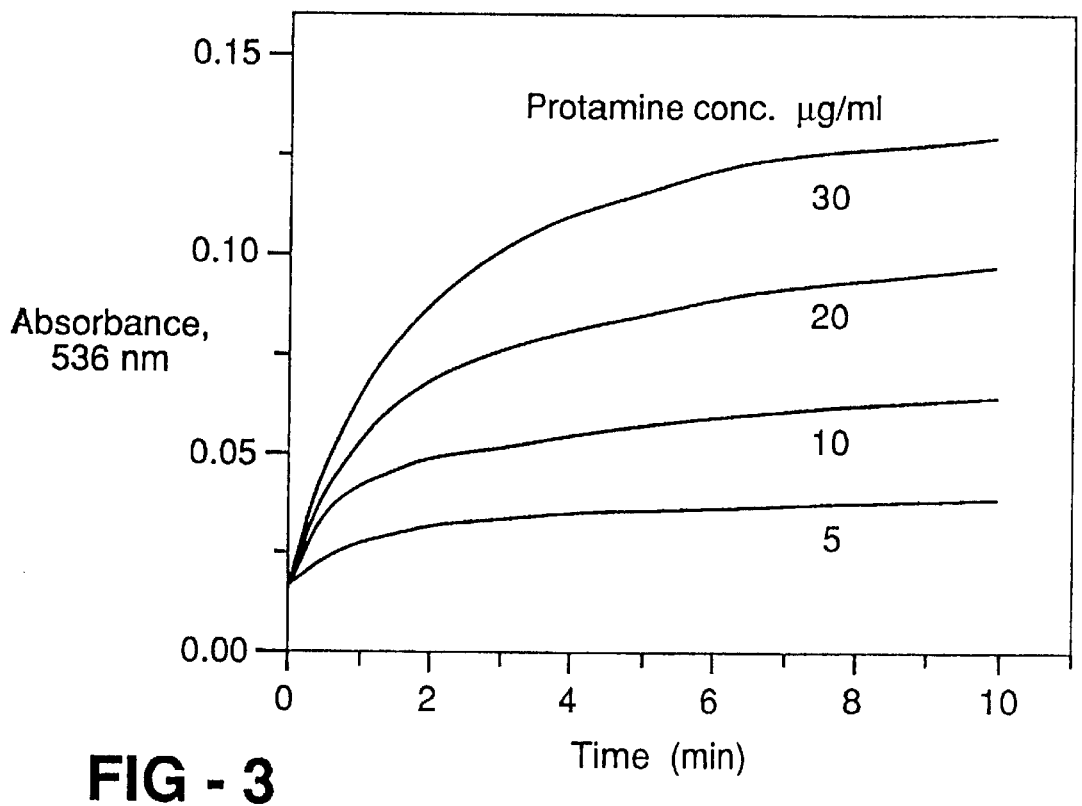
FIG. 3. Absorbance changes of a 2,7-DCFOE sensing film with time, when contacted (non-stirring mode) with protamine at pH 7.4 for the film composition of FIG. 1.
Figure 4:
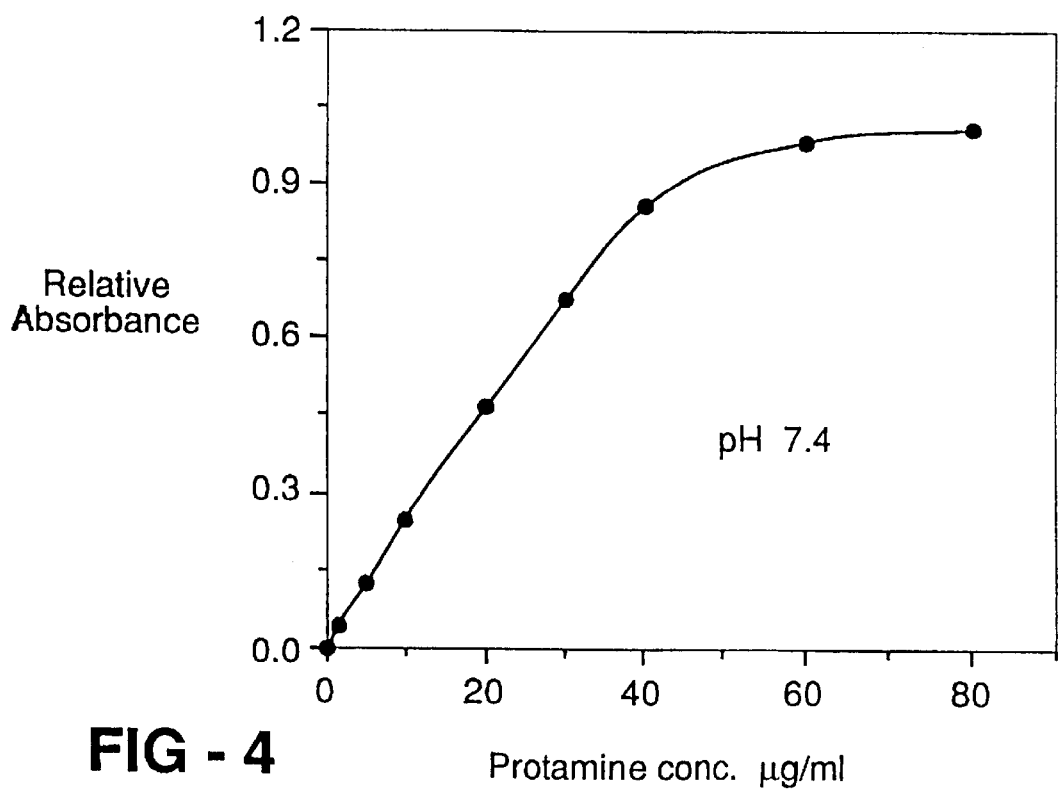
FIG. 4. A typical protamine sensing curve obtained in a non-stirring mode at pH 7.4 for a 2,7-DCFOE film for the film composition of FIG. 1. Film absorbance: 536 nm. Contacting time: 3 min.

When the film is in contact with protamine solutions without convection (in static, non-stir), there is a significant absorbance increase during the initial 2 minutes, after which the polycation detection film absorbance change is much slower. FIG. 3 shows the absorbance changes of a 2,7-DCFOE membrane film with time recorded at four representative concentration levels. The film response is faster as the protamine concentration in the buffer solution increases. With low protamine concentrations (1–15 $\mu$g/ml with a film of 2 $\mu$m), after the initial first minute, the film absorbance changes very little, even over a period of 24 h. In addition, at these low concentrations, the film response does not depend on the film thickness (d >2 $\mu$m) and sample volume. This shows that the membrane response depends to a great extent on the mass transport of protamine from the bulk of the solution to the film interface. The rate of mass transport to the surface of the film, in turn, is controlled by both convection within the bulk of the sample solution (i.e., via stirring) and diffusion through a stagnant Nernst diffusion layer adjacent to the surface of the polymer film. Without convection, the concentration depletion at the Nernst diffusion layer is quickly developed, and it increases as the concentration becomes lower. The film absorbances at 3 min response time vs. the protamine concentration are shown in FIG. 4. The whole calibration is done with the same film, and the film is treated with a pH 4.40 phosphate buffer before the next measurement. These results indicate that under static conditions analytically useful optical signals are obtained within 3 min.

Due to their macrosize and high charge, the equilibrium responses of polycations are slow and insensitive. However, by utilizing a kinetic response mode, high sensitivity and good reproducibility for protamine detection is achieved within a reasonable time frame by the instant invention. In addition to aqueous solution, the films described herein are also useful for the detection of protamine and heparin in diluted serum and whole blood. The use of controlled stirring lowers the detection limits achievable for applications where low protamine excess can be detected (e.g. protamine: ~10 $\mu$g/ml [18, 21]). Since the membrane films are easily reversed by low pH buffers after each measurement, the film is useful to monitor the protamine levels during various processes via flow-injection method.

The following examples are given for the purpose of illustrating various embodiments of the invention and are not meant to limit the instant invention, as recited in the appended claims in any fashion.

EXAMPLE 1

Reagents

Bis(2-ethylhexyl) sebacate (DOS), fluorescein, 4,5-dibromofluorescein, 2,7-dichlorofluorescein, 1-iodooctadecane, 4,5-dibromofluorescein octadecyl ester, tetrahydrofuran (THF), and high molecular weight poly (vinyl chloride) (PVC) are obtained from Fluka (Ronkonkoma, N.Y.). 1-Bromodecosane, fluoresceinamine and azura A are purchased from Aldrich Chemical Co. (Milwaukee, Wisc.). Tecoflex polyurethane (PU, SG-80A) is obtained from Thermedics, Inc. (Woburn, Mass.).

Protamine sulfate (from Herring, grade III and from salmon, grade X), poly-L-lysine hydrobromide (MW=1,000–4,000 and 4,000–15,000), poly-L-arginine hydrochloride (MW 5,000–15,000), trypsin and solid heparin (sodium salt from porcine intestine mucosa, 169 USP units/mg), N-[2-hydroxyethyl]piperazine-N'2-ethanesulfonic acid (HEPES), and frozen calf serum are purchased from Sigma (St. Louis, Mo.). All other chemicals are commercially available products. Standard solutions and buffers are prepared with distilled-deionized water.

EXAMPLE 2

Synthesis of 2,7-dichlorofluorescein Octadecyl Ester (DCFOE)

A mixture of 2,7-dichlorofluorescein (430 mg, 1.07 mmol) and 1-iodooctadecane (380 mg, 1 mmol) in 5 ml of DMSO and $K_2CO_3$ solid (290 mg, 2.1 mmol) is stirred in an oil bath at 65° C. for 20 h. The red precipitate that formed upon addition of 10 ml saturated NaCl is filtered, washed with deionized water and redissolved in ethyl acetate with 1 M HCl. The yellow orange, organic phase is separated, washed with phosphate buffer (pH 7.4) and deionized water and evaporated to dryness under reduced pressure. The product is recrystallized twice with acetone to yield pure DCFOE. Yield: 470 mg, 72%. Reverse phase RP-TLC: Rf=0.65 (octadecylsilane-modified reversed-phase silica plates (KC18F, Whatman, N.J.), ethanol-water (90:10) as eluent). $^1$H NMR ($CD_3COOD/CDCl_3$), 8.34–8.31 (d. J=8. 1H, aromatic), 7.80–7.76 (m, 2H, aromatic), 7.47–7.,44 (d, J=7, 1H, aromatic), 7.20 (S, 2H, aromatic), 7.12 (S, 2H, aromatic), 4.02–3.98 (t, J=8, 2H, OCH2), 1.34–1.13 (m. 32H, aliphatic $CH_2$), 0.89–0.87 (t. J=7, 3H, $CH_3$). IR (KBr, 3400 $cm^{-1}$, 1709 $cm^{-1}$), Elemental analysis: Anal. Calcd: $C_{38}H_{46}Cl_2O_5$: C, 69.90, H, 7.05, Cl, 10.85. Found: C, 69.87, H, 7.11, Cl, 10.76.

EXAMPLE 3

Synthesis of 2,7-dichlorofluorescein Docosyl Ester (DCFDE)

The procedure of Example 2 is repeated with 1 mmol of 1-iodedocosane in place of 1-iodooctadecane. Recrystallization yielding purified DCFDE.

EXAMPLE 4

Synthesis of Fluoresceinamine Docosylate

The procedure of Example 2 is repeated with 1.07 mmol (298 mg) of fluoresceinamine in place of the 2,7-dichlorofluorescein. The purified product is obtained at 78% yield.

EXAMPLE 5

Polymer Film Preparation

PVC/PU membrane films result from mixing between about 0.1 and 10% chromoionophore, with 1.0 wt. % of chromoionophore being preferred; and between about 15 wt. % and 45 wt. % of polymer, with 30 wt. % being preferred of polymer (10–25 wt. % of PVC and 20–5 wt. % of PU). DOS is used as plasticizer. The film casting solutions were prepared by dissolving a total amount of 200 mg of film components in 2 ml of THF. Films of preferably about 1–3 $\mu$m thickness are cast from these solutions onto glass slides (1×5×0.1 $cm^3$) by spin coating, however films of between 0.5 to about 25 $\mu$m are operable herein.

EXAMPLE 6

Absorbance Measurements

Absorbance measurements are made on a UV/Vis double beam spectrophotometer (Lambda 6B, Perkin Elmer) with the polymer film coated glass slides placed against the inner wall of a commercial quartz cell (1×1×4.4 $cm^3$) with the film facing the test solution. All quantitative measurements are made at 536 nm. The films are soaked for ca. 20 min. in a HEPES buffer (pH 7.4) until the membrane had a stable absorbance value before the first protamine measurement is made. Sample solutions with various protamine concentrations are prepared by adding aliquots of a standard protamine solution to a fixed volume of buffer (0.05 M HEPES or phosphate, pH 6.0 to 7.4). All protamine tests are done with grade III protamine unless stated otherwise. Calibration in the non-stir mode is performed by placing the films in 3 ml of the protamine sample solution in the standard cuvette. The absorbances are taken at predetermined time intervals. The equilibrium responses are obtained using a 20 ml test solution stirred electromagnetically for 1 h, and then the film and test solution is transferred into a standard cuvette for the absorbance measurement. The spectrophotometer is adjusted using the absorbance of a sensing film at 700 nm as zero. Optical response of the films toward other small cations are measured in the corresponding chloride solution buffered to pH 7.40. All measurements and pre-equilibrations are carried out under ambient conditions (23–24° C.).

EXAMPLE 7

Titration of Heparin

The experiment is conducted by first dissolving a known amount of heparin in 10 ml of HEPES buffer (pH 7.4). Aliquots of a protamine standard solution are then added step-wise. After each addition of protamine, the film is dipped into the test solution for 3 min, and then immediately transferred to the cuvette containing only buffer for the absorbance measurement at 536 nm.

EXAMPLE 8

Protamine Response in Diluted Serum

The response of a membrane film in serum samples is done using diluted serum as a background. For the film composition of FIG. 1, a constant pH of 7.4 is assured by diluting the serum with HEPES buffer of pH 7.4 in a serum to buffer ratio of 1:3. The sensing film is placed in the diluted serum for 3 min immediately after an aliquot of protamine is added. The film is then transferred to the cuvette containing only buffer for absorbance measurement. Both the test samples and standard curve are prepared using the same serum.

EXAMPLE 9

Protamine Measurement in Serum by Azure-Heparin Assay

The quantity of protamine in serum is verified using the azure A dye method according to Yang et al. [21]. The test samples are parallel to the protamine concentrations for the film method. The dye method is done by placing 2 ml of azure A (80 $\mu$g/ml) and 1 ml of heparin (120 $\mu$g/ml) solution into a methylacrylate standard cuvette; then 1 ml of serum containing protamine in the range of 40–160 mg/ml was added. The absorbance at 620 nm of each solution is measured against the solution with the same background contains no protamine. Both the test samples and standard curve are prepared using the same serum.

EXAMPLE 10

Response of an Invention Film to Polycations Other Than Protamine

Figure 5:
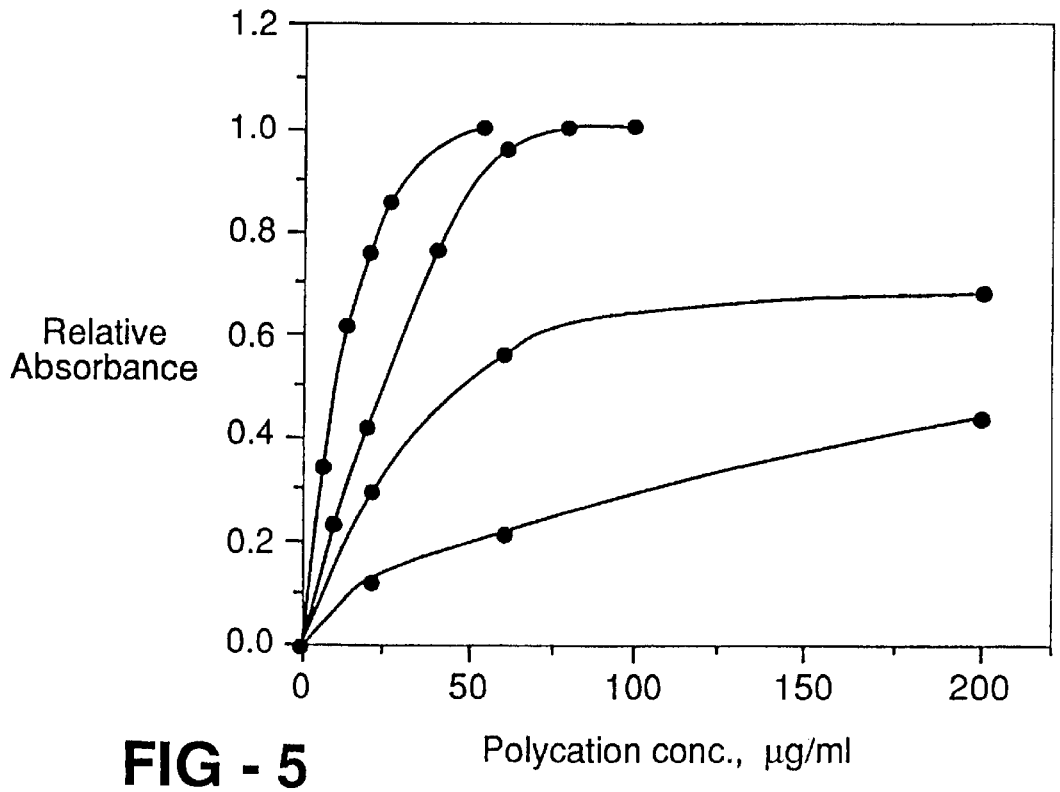
FIG. 5. Optical response of a 2,7-DCFOE sensing film to different polycations at pH 7.4 for the film composition of FIG. 1. (○) poly-L-arginine, (●) protamine grade X, (□) poly-L-lysine, MW=4,000–15,000, (▲) poly-L-lysine, MW=1,000–4,000. Contacting time: 3 min (non-stirring).

Although much of the testing of the instant invention utilized a Herring grade III protamine, a protamine sample obtained from salmon grade X also gives a comparable response in terms of speed and sensitivity. Poly-L-arginine, with more guanadinium groups than a protamine of similar polymer weight [17], interacts with the instant invention so as to be detectable by changing the color of the membrane film (maximum absorbance at 536 nm). The film optical response toward commercial poly-L-arginine with molecular weight between 5000–15000 daltons is greater than that towards protamine (FIG. 5) in the same time frame and mass concentration in a non-stirred solution for a 2,7 DCFOE film. In addition, membranes loaded with poly-L-arginine do not reverse easily. This shows that the film extraction of poly-L-arginine is even more favorable than protamine, given the fact that larger molecules have a smaller diffusion coefficient. In contrast, the monomer, L-arginine, showed no response, even at concentration as high as 0.2 M.

Poly-L-lysine, a polycation at neutral pH, has also been used previously as heparin antagonist [25]. Interestingly, this polymer has molecular sizes comparable to protamine and poly-L-arginine but comparatively shows a lesser optical response over the same time period (see FIG. 5) but nonetheless is detectable. Smaller molecular weight fractions show an even slower response than larger ones. A membrane film of the instant invention becomes pink (fully complexed, $\lambda_{max}$=536 nm. $\alpha$=1) after it is in contact with 200 µg/mL poly-L-lysine solution for 3 h (3 min. for protamine and poly-L-arginine). This result indicates that the extraction of poly-L-lysine into the film is slow and less favorable than protamine and poly-L-arginine, and thus a membrane film of the instant invention has applications in differentiating between different types of polycations.

EXAMPLE 11

Response of an Invention Film to Small Cations

Biological and/or physiological samples generally contain small cations, such as $Na^+$, $K^+$, $NH_4^+$, $Li^+$, $Mg^{2+}$, $Ca^{2+}$. To apply the polycation sensing film in biological systems, it is necessary to know whether these common cations have any interference. The small cation interference is evaluated by monitoring the film absorbance at 536 nm in buffer solutions of pH 7.4 (0.05 M HEPES adjusted with 1 M KOH) containing various chloride salts. The results all expressed in relative absorbance calculated with equation 2 are listed in Table 1. The data show that these small cations have no significant response at concentrations below 0.01 M. For monovalent cations with concentrations as high as 0.1 M, the optical responses are still negligible ($\alpha$<0.05). Generally, in physiological samples the concentrations of these common cations are below 0.01 M (0.1 M for $Na^+$), therefore, they will not interfere the optical detection of protamine.

EXAMPLE 12

Repeatability and Life Time of an Invention Sensing Film

The repeatability of a sensing film is evaluated by measuring the optical absorbance of the membrane film in contact with 40 µg/ml of protamine solution for 3 min. After each measurement, a membrane film operating near neutral pH is regenerated by dipping it in a pH 4.40 buffer for 30 seconds. The sensing membrane exhibits good repeatability (RSD <5%, n=10). No detectable amount of dye was found in the buffer solutions for both conditioning the film and protamine response when the dye content less than 1 wt. %. However, the film absorbance dropped to 80% of the initial value after repeated for over 100 cycles (sensing and regeneration) over two weeks. The membrane can be stored in dark in either dry or wet conditions without losing its sensitivity for at least one month.

2',7'-dichlorofluorescein docosyl ester (DCFDE) containing 4 more $CH_2$ groups in its side chain demonstrates slightly higher lipophilicity than DCFOE. Membrane films with DCFDE demonstrate slightly better reproducibility under the aforementioned test conditions. The spectra, response curve of DCFDE films of the instant invention in both stir and non-stir modes and the pH influence are similar to those membranes doped with DCFOE.

EXAMPLE 13

Repeatability and Life Time of an Acidic Invention Sensing Film

The docosylate of 2,7-dichlorofluorescein amine (isomer I) is the active component of a sensing film operative between pH 3.0 and 4.0 and preferably at pH 3.3. The procedure of Example 12 is followed with regeneration occurring using pH 2.0 buffer, with similar results.

EXAMPLE 14

Colorimetric Titration of Heparin with Protamine

One of the applications of the instant invention is its use as an end point indicator in the process of heparin titration with protamine, given the fact that the film has a very low detection limit (2 µg/ml). The titration is done by dissolving 1 or 2 mg of heparin in 10 ml phosphate or HEPES buffer (pH 7.4), and protamine is stepwisely added into it. After each addition, the protamine sensing film is allowed to contact the solution mixture for 3 min; the absorbance is then measured in a separate cuvette with contains only buffer. A typical titration curve shows inflection at the end point. Results of titrating 1 and 2 mg heparin with protamine shows an average reaction stoichiometry between heparin and protamine in a 1 to 1.36±0.05 weight ratio (n=3), which is close to that reported previously by Yun et al. [23].

EXAMPLE 15

Protamine Response in Diluted Serum

Figure 6:
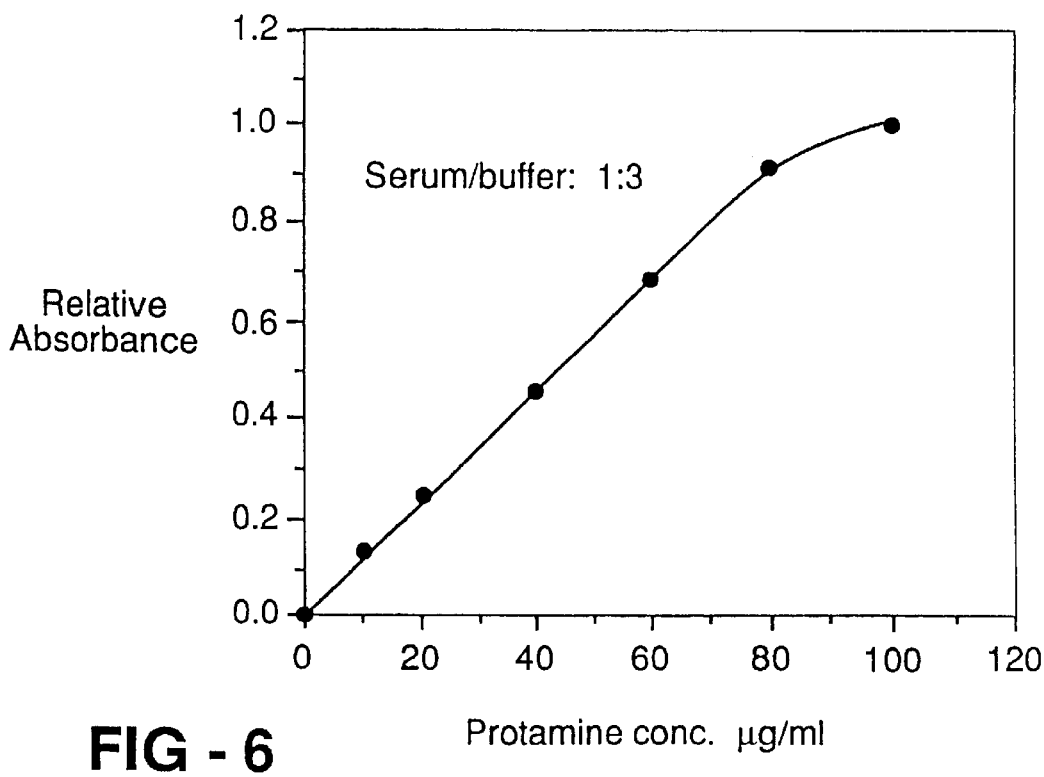
FIG. 6. Response curve of a 2,7-DCFOE sensing film to protamine in diluted serum for the film composition of FIG. 1. Response time: 3 min (non-stirring). Serum:buffer=1:3.

Films of the instant invention are also suitable for sensing polycations within a serum sample. To ensure a constant pH, the responses are made by mixing the serum with a pH 7.40 phosphate buffer. The film absorbance is measured before and after contact with a diluted serum sample. The protamine in serum sample is verified according to Yang et al., using the protamine-heparin-azure competitive binding assay [21]. A film responds to increasing amounts of protamine in a commercial calf serum sample. No absorbance change or distorting of film function in buffer after contact with serum is observed. Response of the film to protamine in diluted serum, as shown in FIG. 6, is smaller than in aqueous solutions (refer to FIG. 4). The optical response is much smaller when the film is placed in the diluted serum sample 10 min after protamine is added. Thus, the above calibration curve is done by placing the membrane film in the diluted serum sample for three minutes immediately after protamine is added. Using the above calibration curve, the protamine level in the same serum sample, measured by the film in the range of 10–40 mg/ml (40–160 µg/ml original serum), is close to the values obtained with the azure-A-heparin colorimetric assay (Table 2). The optimal range for the dye method with heparin of 36 µg/ml (6 U) 30 µg/ml in this study) is 80 to 200 µg/ml with an error of 6% [21].

Similar to the response in aqueous solution, when stoichiometric amount of heparin is added to the protamine serum solution, no optical response is observed due to the protamine-heparin complexation reaction. This result indicates a film of the instant invention has application as an indicator for heparin detection via protamine titration in diluted serum.

Protamine polycations can also be decomposed enzymatically by trypsin [21, 23]. The optical sensing film described herein also has application to monitor this enzymatic process. The specifics of this methodology follow from the information provided within this specification.

EXAMPLE 16

Protamine Response in Whole Blood

Figure 7:
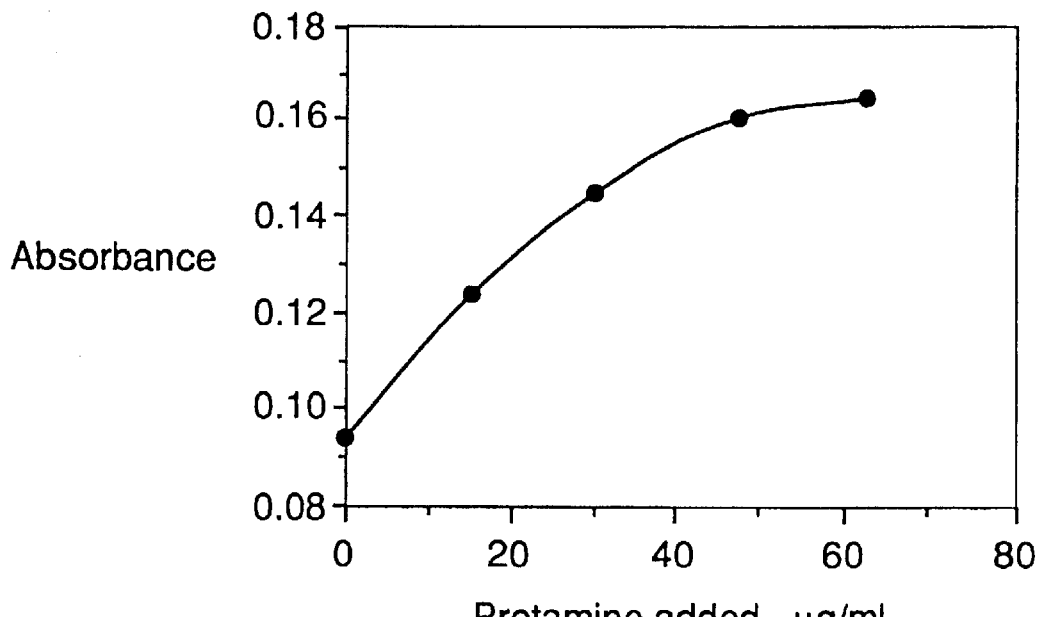
FIG. 7. Response curve of a 2,7-DCFOE sensing film to protamine in citrated whole blood for the film composition of FIG. 1. Response time: 5 min (non-stirring).

Films of the instant invention are also suitable for sensing protamine within whole blood. The whole blood pH is not altered for detection, however citrate salt is added in a quantity sufficient to prevent coagulation. The film responds to increasing amounts of protamine in a commercial calf whole blood sample. No absorbance change or distorting of film function in buffer after contact with whole blood is observed. Response of the film to protamine in whole blood is shown in FIG. 7. The optical response is much smaller when the film is placed in the blood sample 10 minutes after protamine is added. Thus, the calibration curve is done by placing the membrane film in a whole blood sample for 5 minutes immediately after protamine is added. A response similar to that observed in Example 13 is noted when sensing protamine in a whole blood sample.

EXAMPLE 17

Heparin-protamine Titration Response in Whole Blood

Figure 8:
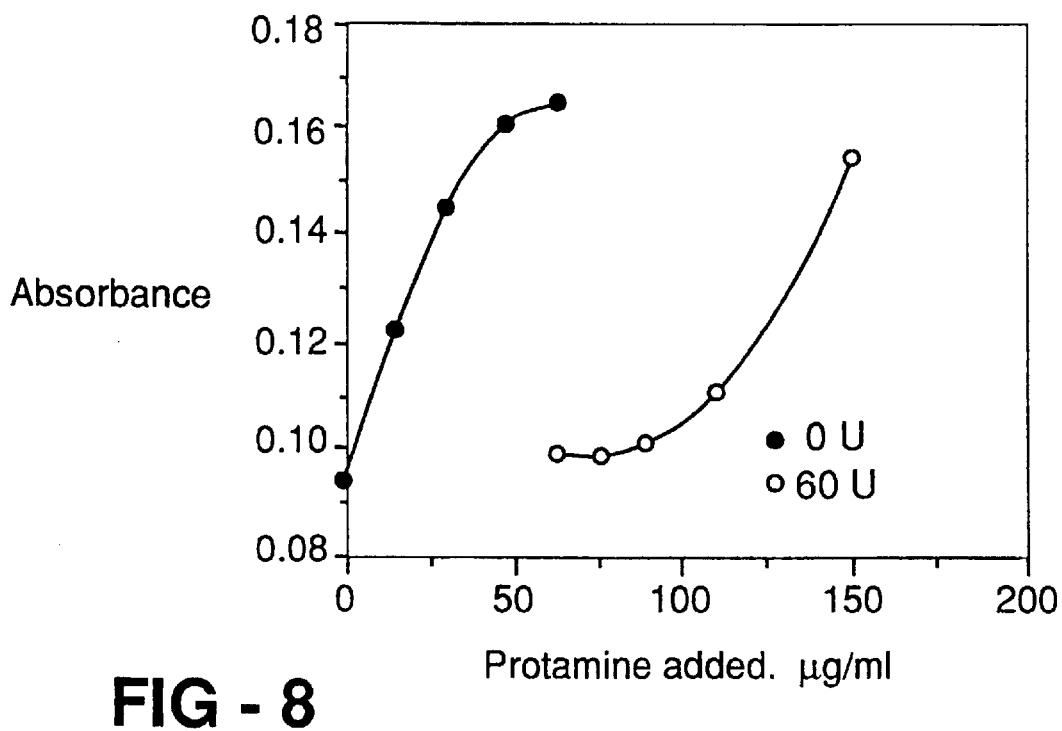
FIG. 8. Response curve of the film of FIG. 7 as an indicator for heparin-protamine titration in whole blood; (●) 0 μg heparin present, 360 μg/ml heparin present.

The membrane film and procedure of Example 14 is duplicated. 60 U (360 $\mu$g/ml) of heparin is added to the whole blood sample, then protamine is added to 60 $\mu$g/ml. An optical response is not observed due to the protamine-heparin complexation reaction. Upon introduction of additional quantities of protamine, the optical response is observed to return to optical response values consistent with uncomplexed protamine. From the response curve associated with addition of protamine to a heparin containing whole blood sample, the film is useful as an indicator for heparin detection via protamine titration in whole blood, as shown in FIG. 8.

EXAMPLE 18

Protamine-trypsin Titration Response in Whole Blood

The film and procedure of Example 15, with substitution of trypsin for heparin. An optical response curve is generated from which the film is acting as an indicator for trypsin detection via protamine decomposition in whole blood.

Any publications mentioned in this specification are indicative of the levels of those skilled in the art to which the invention pertains. These publications are herein incorporated by reference to the same extent as if each individual publication was specifically and individually indicated to be incorporated by reference.

REFERENCES

[1] O. S. Wolfbeis, Fresenius J. Anal. Chem., 337 (1990) 522.
[2] W. Simon, W. E. Morf, K. Seiler and U. E. Spichiger-Keller, Frensenius J. Anal. Chem., 337 (1990) 26.
[3] K. Wang, K. Seiler, B. Rusterholz and W. Simon, Analyst, 117 (1992) 57.
[4] E. Wang, K. Ohashi and S. Kamata, Chem. Lett., (1992) 939.
[5] K. Suzuki, K. Tohda, Y. Tanda, H. Ohzonra, S. Nishiham, H. Inoue and T. Shirai, Anal. Chem., 61 (1989) 382.
[6] J. F. Alder, D. C. Ashworth, R. Narayanaswamy, R. E. Moss and I. O. Sutherland, I. O. Analyst, 112 (1987) 1191.
[7] D. C. Ashworth, H. P. Hung and R. Narayanaswamy, Anal. Chim. Acta, 213 (1988) 251.
[8] K. Seiler and W. Simon, Anal. Chim. Acta, 266 (1992) 73.
[9] K. Suzuki, H. Ohzora, K. Tohda, K. Miyazaki, K. Watanabe, H. Inoue, and T. Shirai, Anal. Chim. Acta, 237 (1990) 155.
[10] M. Lerchi, E. Bakker, B. Rusterholtz and W. Simon, Anal. Chem., 64 (1992) 1534.
[11] M. Lerchi, E. Reitter, W. Simon and E. Pretsch, Anal. Chem., 64 (1994) 1713.
[12] E. Bakker and W. Simon, Anal. Chem., 64 (1992) 1805.
[13] S. S. S. Tan, P. C. Hauser, N. A. Chaniotakis, G. Suter and W. Simon, Chimia, 43 (1989) 257.
[14] S. S. S. Tan, P. C. Hauser, K. Wang, K. Fluri, K. Seiler, B. Rusterholtz, G. Suter, M. Kruettli, U. E. Spichiger and W. Simon, Anal. Chim. Acta, 225 (1991) 35.
[15] E. Wang and M. E. Meyerhoff, Anal. Chim. Acta, 283 (1993) 673.
[16] E. Wang, M. E. Meyerhoff and Y. C. Yang, Anal. Chem., 67 (1995) 522.
[17] H.-G. Elias, Macromolecules 2: Synthesis. Materials and Technology, 2nd., Plenum Press, New York, 1984, Chap. 29.
[18] L. B. Jaques, Pharm. Rev., 31(1980) 99.
[19] N. J. Lowry, O. H. Rosebrugh, A. L. Farr and R. J. Randall, J. Biol. Chem., 193 (1951) 265.
[20] M. M. Bradford, Anal. Biochem., 72 (1976) 248.
[21] V. C. Yang, Y.-Y., Fu, C.-L. C., Teng, S.-C. Ma and J. N. Shanberge, Thrombosis Research, 74 (1994) 427.
[22] B. Fu, E. Bakker, J. H. Yun, V. C. Yang and M. E. Meyerhoff, Anal. Chem., 66 (1994) 2250.
[23] J. H. Yun, M. E. Meyerhoff and V. C. Yang, Anal. Biol. Chem., 224 (1995) 212.
[24] D. C. Neckers, J. Photochem. Photobiol., 47A (1989) 1.
[25] X. Ma, S. F. Mohammad and S. W. Kim, J. Colloids Interface Sci., 147 (1991) 251.

One skilled in the art will readily appreciate that the present invention is well adapted to carry out the objects and provide the applications mentioned, as well as those inherent therein. The present examples along with methods, procedures, specific compounds and molecules described herein are presently representative of preferred embodiments, are exemplary and not intended as limitations on the scope of the invention. Modifications and variations within the spirit of the invention will occur to those skilled in the art. Such modifications are also intended to fall within the scope of the appended claims.

What is claimed is:

1. A membrane film for optical sensing of a molecular species comprising: a lipophilic ester of a compound having a formula:

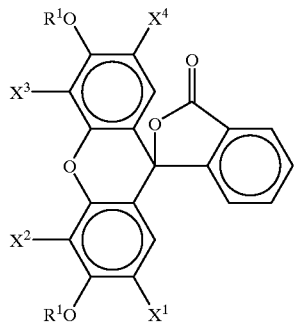

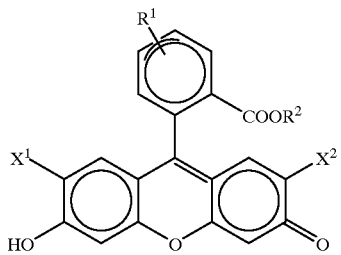

where $X^1$ is selected from the group consisting of: a hydrogen atom, a chlorine atom, and a bromine atom, where $X^2$ is selected from the group consisting of: a hydrogen atom, a chlorine atom, and a bromine atom, where $X^3$ is selected from the group consisting of a hydrogen atom, a chlorine atom, and a bromine atom, where $X^4$ is selected from the group consisting of a hydrogen atom, a chlorine atom, and a bromine atom and at least one of $X^1$, $X^2$, $X^3$ and $X^4$ is a hydrogen atom, and where $R^1$ is selected from the group consisting of: an alkyl having from 14 to 30 carbon atoms, an alkenyl having from 14 to 30 carbon atoms, a haloalkyl having from 14 to 30 carbon atoms, and a haloalkenyl having from 14 to 30 carbon atoms wherein in response to the polycation said ester exhibits an optical response; and an optically inert polymer in which said ester is mixed.

2. The film of claim 1, wherein the molecular species is a polycation.

3. The film of claim 2, wherein the polycation is selected from the group consisting of protamine, poly-L-arginine, and poly-L-lysine.

4. The film of claim 2, wherein the polycation is protamine.

5. The film of claim 1 wherein $X^1$ and $X^2$ are the same type of atom and $X^3$ and $X^4$ are the same type of atom.

6. The film of claim 1 wherein R is an alkyl having an even number of carbon atoms, the number of carbon atoms being greater than 15 and less than 25.

7. The film of claim 1 wherein said ester is maintained at a pH greater than 6.00 and less than 10.00 during exposure to the polycation.

8. The film of claim 6 wherein the pH is maintained between 7.00 and 8.50.

9. The film of claim 7 wherein the pH is maintained between 7.3 and 7.5.

10. The film of claim 1 wherein said ester is present from about 0.1 to about 10 weight percent relative to total film weight.

11. The film of claim 1 wherein said optically inert polymer is present from about 15 weight percent to about 45 weight percent based on total film weight.

12. The film of claim 11 wherein said polymer is a mixture of poly(vinyl chloride) and polyurethane.

13. The film of claim 12 wherein the film has a thickness of from about 0.5 to about 25μ.

14. A membrane film for optical sensing of a molecular species comprising: a lipophilic molecule having the formula:

where $X^1$ is selected from the group consisting of: a hydrogen atom, a chlorine atom, and a bromine atom, where $X^2$ is selected from a group consisting of: a hydrogen atom, a chlorine atom, and a bromine atom, and at least one of $X^1$ and $X^2$ is a hydrogen atom, where $R^1$ is selected from the group consisting of an alkyl having from 10 to 30 carbon atoms, an alkenyl having from 10 to 30 carbon atoms, a haloalkyl having from 10 to 30 carbon atoms and a haloalkenyl having from 10 to 30 carbon atoms, where $R^2$ is selected from the group consisting of: a hydrogen atom, an alkyl having from 10 to 30 carbon atoms, an alkenyl having from 10 to 30 carbon atoms, a haloalkyl having from 10 to 30 carbon atoms and a haloalkenyl having from 10 to 30 carbon atoms, wherein in response to the polycation said molecule exhibits an optical response; and an optically inert polymer in which said molecule is mixed.

15. The film of claim 14, wherein the molecular species is a polycation.

16. The film of claim 15, wherein the polycation is selected from the group consisting of protamine, poly-L-arginine, and poly-L-lysine.

17. The film of claim 15, wherein the polycation is protamine.

18. The film of claim 14, wherein $R^1$ is an alkyl having an even number of carbon atoms, the number of carbon atoms being greater than 15 and less than 25.

19. The film of claim 14, wherein $R^2$ is an alkyl having an even number of carbon atoms, the number of carbon atoms being greater than 15 and less than 25.

20. The film of claim 14, wherein said molecule is maintained at a small pH greater than 3.0 and less than 4.7 during exposure to the polycation.

21. A process for optical titration of heparin comprising the steps of: (a) immersing the film of claim 1 in a solution containing heparin, said solution being buffered to fixed pH; (b) adding an increment of protamine to said solution; (c) providing time for the film to respond to said increment of protamine; and (d) monitoring film absorbance after adding said increment of protamine.

22. The process of claim 21 wherein said solution is buffered to a pH between about 7.0 and 8.4.

23. The process of claim 21 wherein said solution is buffered to a pH between about 3.0 and 4.7.

24. The process of claim 21 further comprising repeating of steps (a)–(d).

25. The process of claim 21 wherein said solution is blood serum.

26. The process of claim 21 wherein said solution is whole blood.

* * * * *